(12) United States Patent
Del Río Pericacho et al.

(10) Patent No.: US 10,221,141 B2
(45) Date of Patent: Mar. 5, 2019

(54) METHOD FOR THE PREPARATION OF HIGHLY PURE IVABRADINE BASE AND SALTS THEREOF

(71) Applicant: URQUIMA, S.A., Palau Solità i Plegamans, Barcelona (ES)

(72) Inventors: José Luis Del Río Pericacho, Barcelona (ES); Yolanda Arredondo Martínez, Barcelona (ES)

(73) Assignee: URQUIMA, S.A., Barcelona (ES)

( * ) Notice: Subject to any disclaimer, the term of this patent is extended or adjusted under 35 U.S.C. 154(b) by 0 days.

(21) Appl. No.: 15/735,172

(22) PCT Filed: Jun. 2, 2016

(86) PCT No.: PCT/EP2016/062533
§ 371 (c)(1),
(2) Date: Dec. 9, 2017

(87) PCT Pub. No.: WO2016/193386
PCT Pub. Date: Dec. 8, 2016

(65) Prior Publication Data
US 2018/0162820 A1 Jun. 14, 2018

(30) Foreign Application Priority Data

Jun. 3, 2015 (EP) .................................. 15382293

(51) Int. Cl.
| | | |
|---|---|---|
| *C07D 223/10* | (2006.01) | |
| *C07D 223/16* | (2006.01) | |
| *C07C 217/74* | (2006.01) | |
| *C07C 309/25* | (2006.01) | |

(52) U.S. Cl.
CPC .......... *C07D 223/16* (2013.01); *C07C 217/74* (2013.01); *C07C 309/25* (2013.01); *C07D 223/10* (2013.01); *C07B 2200/13* (2013.01); *C07C 2602/06* (2017.05); *C07C 2602/42* (2017.05)

(58) Field of Classification Search
CPC .................................................... C07D 223/10
See application file for complete search history.

(56) References Cited

U.S. PATENT DOCUMENTS

2014/0163220 A1    6/2014    Carranza

FOREIGN PATENT DOCUMENTS

| | | |
|---|---|---|
| CN | 101671265 | 3/2010 |
| CN | 101857549 | 10/2010 |
| CN | 102249937 | 11/2011 |
| CN | 102372642 | 3/2012 |
| CN | 102408346 | 4/2012 |
| CN | 103524360 | 1/2014 |
| CN | 104262179 | 1/2015 |
| CN | 104557573 | 4/2015 |
| CN | 104829470 | 8/2015 |
| EP | 0 534 859 A1 | 3/1993 |
| EP | 2 495 237 A1 | 9/2012 |
| EP | 2 740 725 | 6/2014 |
| EP | 2 740 725 A1 | 6/2014 |
| WO | WO 2005/110993 A1 | 11/2005 |
| WO | WO 2005123659 | 12/2005 |
| WO | WO 2008/065681 A2 | 6/2008 |
| WO | WO 2008065681 | 6/2008 |
| WO | WO 2009062377 | 5/2009 |
| WO | WO 2009153461 | 12/2009 |
| WO | WO 2010007253 | 1/2010 |
| WO | WO 2010023383 | 3/2010 |
| WO | WO 2010072409 | 7/2010 |
| WO | WO 2010072930 | 7/2010 |
| WO | WO 2010089475 | 8/2010 |
| WO | WO 2010112704 | 10/2010 |
| WO | WO 2010112705 | 10/2010 |
| WO | WO 2011138625 | 11/2011 |
| WO | WO 2013017937 | 2/2013 |
| WO | WO 2013117869 | 8/2013 |
| WO | WO 2014013179 | 1/2014 |
| WO | WO 2014057228 | 4/2014 |
| WO | WO 2014072640 | 5/2014 |
| WO | WO 2014131996 | 9/2014 |
| WO | WO 2014184501 | 11/2014 |
| WO | WO 2015/022702 A2 | 2/2015 |
| WO | WO 2015022702 | 2/2015 |
| WO | WO 2016079684 | 5/2016 |

OTHER PUBLICATIONS

English language Abstract of EP 0 534 859 A1 (Mar. 31, 1993).
English language Abstract of EP 2 740 725 A1 (Jun. 11, 2014).
International Search Report of PCT/EP2016/062533 dated Dec. 15, 2016.

*Primary Examiner* — Bruck Kifle
(74) *Attorney, Agent, or Firm* — Hershkovitz & Associates, PLLC; Abe Hershkovitz

(57) ABSTRACT

A method for the preparation of purified ivabradine and salts thereof, a method for the purification of ivabradine and salts thereof, a new reactant used in said methods and the use of said reactant for the preparation of ivabradine.

19 Claims, 1 Drawing Sheet

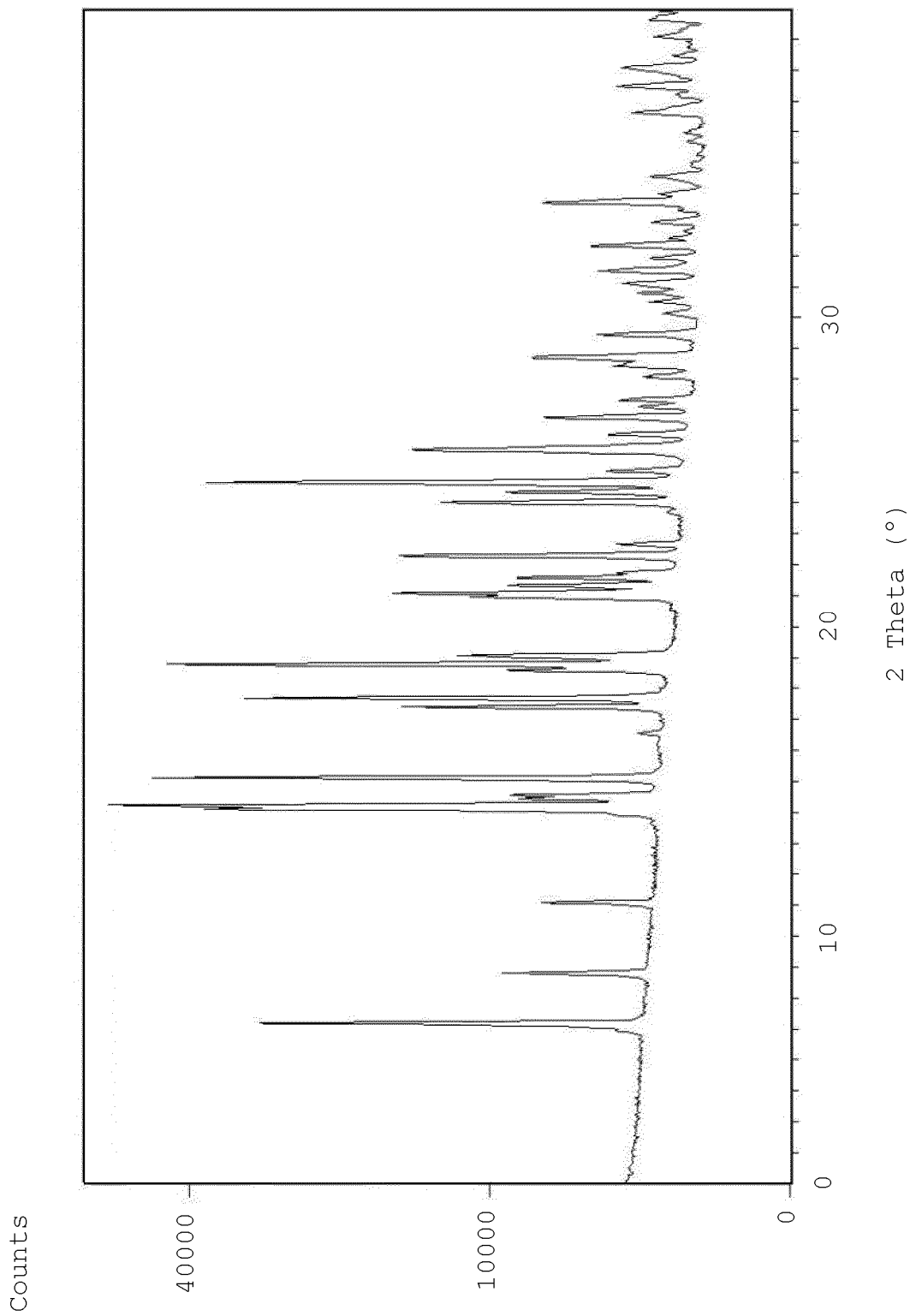

METHOD FOR THE PREPARATION OF HIGHLY PURE IVABRADINE BASE AND SALTS THEREOF

FIELD OF THE INVENTION

The present invention relates to a new method for the preparation of ivabradine and salts thereof.
The invention also relates to new reactant used in the above-mentioned method of preparation and to the use of said reactant for the preparation of ivabradine.

PRIOR ART

Ivabradine (having formula (I)), and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also of various pathologies involving rhythm disturbances, especially supraventricular rhythm disturbances, and in the treatment of heart failure.

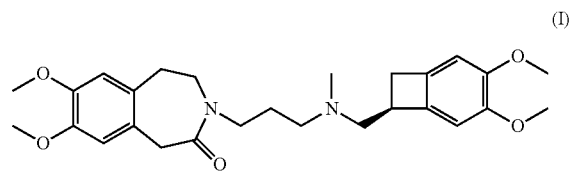
(I)

The preparation and therapeutic use of ivabradine and addition salts thereof with a pharmaceutically acceptable acid, and more especially its hydrochloride, have been described in the European patent specification EP 0 534 859.
The art describes various processes for manufacturing ivabradine using (S)—N-[4,5-dimethoxybenzocyclobut-1-yl)-methyl] N-methylamine of formula (II)

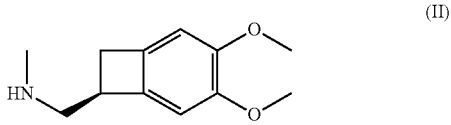
(II)

as an intermediate.
For example WO 2005/110993 A1 describes a process wherein compound of formula (II) is reacted with a compound of formula (IIIa)

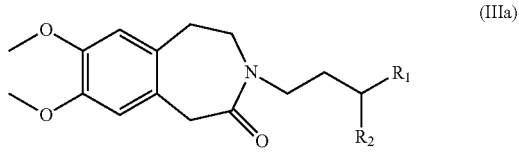
(IIIa)

in the presence of hydrogen and a catalyst.
EP 0 534 859 A1 describes a process wherein compound of formula (II) is reacted with a compound of formula (IIIb)

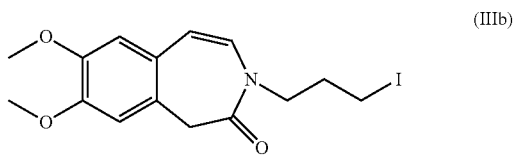 [SMILES: COc1cc2c(cc1OC)CC(=O)N(CCCI)C=C2]
(IIIb)

and the resulting product is subsequently hydrogenated to yield ivabradine.
A disadvantage of the above-mentioned processes, in which a compound of formula (II) is used as a reaction intermediate in the preparation of ivabradine, is that substantial amounts of compound (II) may remain in the reaction media together with the resulting ivabradine and it is difficult to separate said compound (II) from ivabradine unless methods to obtain highly pure chemical compounds such as chromatographic techniques are used. However, the chromatographic technique for purification is cumbersome, tedious and difficult to utilize on an industrial scale.
EP 2 495 237 A1 describes a process for the preparation of highly pure ivabradine hydrochloride by treating crude ivabradine with a derivatizing agent in a suitable solvent followed by isolation of highly pure ivabradine hydrochloride. In the description it is explained that the term "derivatizing agent" is defined as agents which derivatize impurities adhered with the crude ivabradine. The expert in the field understands that derivatizing a compound involves the formation or the change of at least a new covalent bond in the compound. This interpretation is coherent with the disclosure of EP 2 495 237 A1 wherein only categories of derivatizing agents which are mentioned are those comprising any nitrogen or oxygen protecting group.
However, EP 2 495 237 A1 fails to explain in general how the "derivatized" impurities are separated from ivabradine to improve the purity of ivabradine. In the examples of EP 2 495 237 A1 the main impurity is (S)—N-[4,5-dimethoxybenzocyclobut-1-yl)-methyl] N-methylamine (compound of formula (II)), which is one of the reactants used to synthetize ivabradine, and the derivatization converts the secondary amine group of said compound in either an amide (example 1), a carbamate (example 2) or a sulfonamide (example 3). Following this conversion the reaction mixture is treated with hydrochloric acid whereby ivabradine is protonated while the derivatized impurity remains in neutral form. This difference is used to extract the derivatized impurity with an organic solvent.
The technique described in EP 2 495 237 has the drawback that the compound (S)—N-[4,5-dimethoxybenzocyclobut-1-yl)-methyl] N-methylamine (compound of formula (II)), which is one of the reactants used to synthetize ivabradine, is converted into a different derivative by forming a new covalent bond. Thus, if it would be desired to recover the compound of formula (II) the newly formed covalent bond in the newly formed derivative would have to be cleaved and this requires the use of relative harsh conditions.
Therefore, there is a need in the state of the art for alternative methods for the preparation of ivabradine base and salts thereof using processes for manufacturing ivabradine that make use of (S)—N-[4,5-dimethoxybenzocyclobut-1-yl)-methyl] N-methylamine of formula (II) as an intermediate and which allow the purification of ivabradine, the separation of any unreacted amount of the compound of formula (II) from the reaction media and a simple recovery of said compound of formula (II) for its use as a reactant in the process of synthetizing ivabradine.

SUMMARY OF THE INVENTION

An aspect of the present invention is to provide an industrially applicable method for the preparation of highly pure ivabradine base and salts thereof comprising the steps of:

a) providing a starting mixture comprising ivabradine base and at least (S)—N-[4,5-dimethoxybenzocyclobut-1-yl)-methyl] N-methylamine of formula (II)

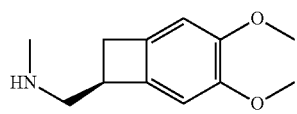

b) treatment of the mixture of step a) with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

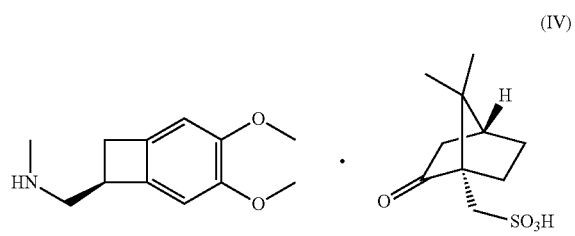

c) separation of the salt of the compound of formula (IV) from the reaction media comprising ivabradine base;
d) isolation of ivabradine base from the solution resulting from step c)
e) optionally converting ivabradine base to the desired salt by addition of the corresponding acid in a suitable solvent (S1).

Another aspect of the present invention is the use of (1S)-(+)-10 camphorsulfonic acid for the purification of ivabradine out of a mixture comprising ivabradine base and (S)—N-[4,5-dimethoxybenzocyclobut-1-yl)-methyl] N-methylamine of formula (II).

Another aspect of the present invention is the use of compound (IV) to retrieve the excess of (S)—N-[4,5-dimethoxybenzocyclobut-1-yl)-methyl] N-methylamine of formula (II) present in the reaction mixture resulting from the condensation, optionally under reductive conditions, of (S)—N-[4,5-dimethoxybenzocyclobut-1-yl)-methyl] N-methylamine of formula (II)

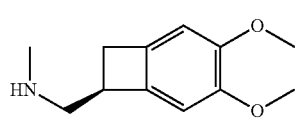

with a compound of formula (III)

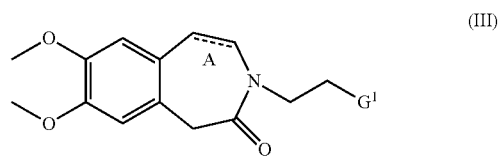

wherein the bond labeled with the letter A is either a single bond or a double bond, $G^1$ is selected from the group comprising —$CH_2$—X (being X an halogen atom, hydroxy, benzenesulfonyloxy, tosyloxy or methanesulfonyloxy group), a —CHO group, a —CN group and a —CH($OR^1$)($OR^2$) group wherein $R^1$ and $R^2$ are independently C1-C8 alkyl groups or $R^1$ and $R^2$ form together a C2-C4 alkylene or a C2-C4 alkenylene group followed by hydrogenation of the condensation product in the case where the bond labeled with the letter A is a double bond in a process to prepare ivabradine through the conversion of compound (IV) to compound (II) which may then be reused in the manufacture of ivabradine.

Another aspect of the present invention is the polymorphic form I of compound of formula (IV).

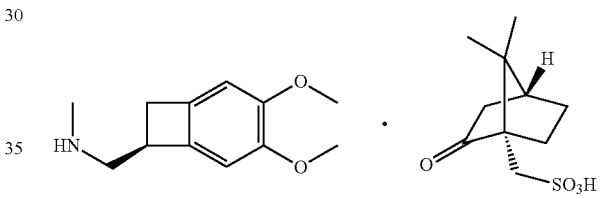

DESCRIPTION OF THE FIGURES

FIG. 1 shows the X-ray diffraction diagram, measured with a copper X-ray source, of polymorphic form I of compound of formula (IV).

DETAILED DESCRIPTION OF THE INVENTION

An aspect of the present invention is to provide an industrially applicable method for the preparation of ivabradine base and salts thereof comprising the steps of:

a) providing starting a mixture comprising ivabradine base and at least (S)—N-[4,5-dimethoxybenzocyclobut-1-yl)-methyl] N-methylamine of formula (II)

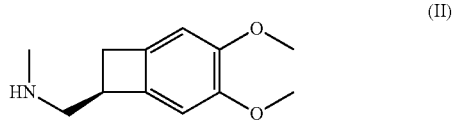

b) treatment of the mixture of step a) with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

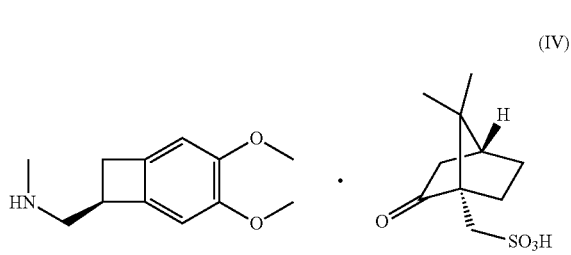

(IV)

c) separation of the salt of the compound of formula (IV) from the reaction media comprising ivabradine base;
d) isolation of ivabradine base from the solution resulting from step c)
e) optionally converting ivabradine base to the desired salt by addition of the corresponding acid in a suitable solvent (S1).

In one embodiment of the present invention after step a) and before step b) the amount of (S)—N-[4,5-dimethoxybenzocyclobut-1-yl)-methyl] N-methylamine of formula (II) in the mixture of step a) is determined and wherein the amount of (1S)-(+)-10 camphorsulfonic acid used in step b) is selected so that the molar ratio of (1S)-(+)-10 camphorsulfonic acid to (S)—N-[4,5-dimethoxybenzocyclobut-1-yl)-methyl] N-methylamine of formula (II) is comprised between 0.5 and 1.5, preferably between 0.5 and 0.9. The extreme of the ranges mentioned in the previous sentence are included in said ranges. In one embodiment of the present invention the mixture of step a) is dissolved or suspended in a suitable solvent (S2). Examples of suitable solvents (S2) are ketones such as acetone and methyl ethyl ketone; alcohols such as methanol, ethanol and isopropanol; nitriles such as acetonitrile; ethers such as tetrahydrofuran; esters such as ethyl acetate, toluene and the like and mixtures thereof, preferably selected from toluene, acetonitrile and mixtures thereof In another embodiment of the present invention (1S)-(+)-10 camphorsulfonic acid is dissolved in a suitable solvent (S3) prior to its addition to the mixture of ivabradine and compound of formula (II). Examples of suitable solvents (S3) are ketones such as acetone and methyl ethyl ketone; alcohols such as methanol, ethanol and isopropanol; nitriles such as acetonitrile; ethers such as tetrahydrofuran; esters such as ethyl acetate, and the like and mixtures thereof, mixtures of the solvents mentioned above with toluene, preferably selected from acetonitrile and mixtures of acetonitrile with toluene.

In one embodiment of the present invention step b) is carried out at a temperature comprised between 0° C. and 30° C., for example between 20° C. and 25° C., between 10° C. and 15° C. or between 0° C. and 5° C.

In one embodiment of the present invention separation of the salt of the compound of formula (IV) from the reaction media comprising ivabradine base is carried out by a process selected from centrifugation and filtration. Filtration may be carried out using, by way of illustration and not limitation, one or more of membrane filtration, surface filtration, depth filtration, screen filtration, and filtration aid, for example.

Isolation of ivabradine base from the solution resulting from step c) may be carried out by concentrating in vacuo to dryness or alternatively adjusting the volume of solvent, or mixtures of solvents, for the next transformation.

Conversion of ivabradine base to the desired salt is carried out by addition of the corresponding acid in a suitable solvent or solvent mixture (S1). Suitable solvents (S1) include but are not limited to ketones such as acetone; alcohols such as methanol, ethanol and isopropanol; nitriles such as acetonitrile; ethers such as tetrahydrofuran; halogenated hydrocarbons such as dichloromethane, dichloroethane and chloroform; esters such as ethyl acetate, toluene, and the like or mixture thereof.

The mixture comprising ivabradine base and at least (S)—N-[4,5-dimethoxybenzocyclobut-1-yl)-methyl] N-methylamine of formula (II) of step a) may be obtained by any suitable method. Advantageously it is obtained by method involving the preparation of ivabradine by condensation of a suitable precursor with (S)—N-[4,5-dimethoxybenzocyclobut-1-yl)-methyl] N-methylamine of formula (II).

In one embodiment the mixture comprising ivabradine base and at least (S)—N-[4,5-dimethoxybenzocyclobut-1-yl)-methyl] N-methylamine of formula (II) is obtained by a method comprising the steps:

a) condensation, optionally under reductive conditions, of (S)—N-[4,5-dimethoxybenzocyclobut-1-yl)-methyl] N-methylamine of formula (II)

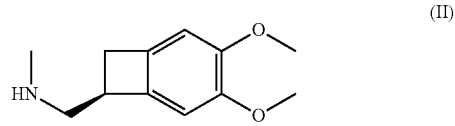

(II)

with a compound of formula (III)

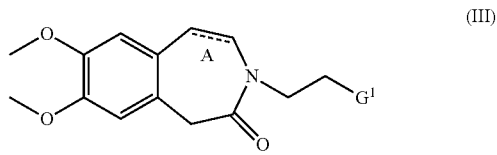

(III)

wherein the bond labeled with the letter A is either a single bond or a double bond, $G^1$ is selected from the group comprising —$CH_2$—X (being X an halogen atom, hydroxy, benzenesulfonyloxy, tosyloxy or methanesulfonyloxy group), a —CHO group, a —CN group and a —CH($OR^1$)($OR^2$) group wherein $R^1$ and $R^2$ are independently C1-C8 alkyl groups or $R^1$ and $R^2$ form together a C2-C4 alkylene or a C2-C4 alkenylene group, b) hydrogenation of the condensation product in the case where the bond labeled with the letter A is a double bond.

In an embodiment of the present invention compound of formula (III) is selected so that the bond labeled with the letter A is a single bond and $G^1$ is a group —$CH_2$—X wherein X is an halogen atom. In a preferred embodiment the reaction of compounds (II) and (III) as defined in the previous sentence is carried out in the presence of a base in polar aprotic or protic solvents. The base can be selected from triethylamine and alkali metal carbonates, bicarbonates and hydroxides and preferably potassium carbonate. The polar aprotic or protic solvent may be selected from tetrahydrofuran, toluene, acetone, acetonitrile, dimethylformamide, dimethylsulfoxide, N-methyl-2-pyrrolidone, water, isopropanol, C1-C4 linear aliphatic alcohols such as methanol, ethanol etc. and mixtures thereof. More preferably, the solvent is dimethylformamide or dimethylsulfoxide or mixture of dimethylformamide with toluene and most preferably the solvent is dimethylformamide or mixture of dimethylformamide with toluene. It is advantageous to use dimethylformamide during condensation reaction because reaction rate is faster. Reaction is conducted at 25-95° C. and preferably at 55-75° C. The completion of reaction can be monitored by high performance liquid chromatography.

In an embodiment of the present invention compound of formula (III) is selected so that the bond labelled with the letter A is a single bond and $G^1$ is selected from the group comprising a —CHO group and a —CH(OR$^1$) (OR$^2$) group wherein $R^1$ and $R^2$ are independently C1-C8 alkyl groups or $R^1$ and $R^2$ form together a C2-C4 alkylene or a C2-C4 alkenylene group. In a preferred embodiment the reductive amination reaction of compounds (II) and (III) as defined in the previous sentence is carried out in the presence of hydrogen an a suitable catalyst. Among the catalysts which can be used in the reductive amination, there may be mentioned, without implying any limitation, palladium, platinum, nickel, ruthenium, rhodium, and their compounds, particularly in supported form or in oxide form, preferably palladium-on-carbon. The temperature of the reductive amination reaction is preferably from 30 to 120° C., more preferably from 40 to 100° C., even more preferably from 60 to 95° C. The hydrogen pressure during the reductive amination reaction is preferably from 1 to 220 bars, more preferably from 1 to 100 bars, even more preferably from 10 to 60 bars.

Another aspect of the present invention is to provide an industrially applicable method for the purification of mixtures comprising ivabradine base and (S)—N-[4,5-dimethoxybenzocyclobut-1-yl)-methyl] N-methylamine of formula

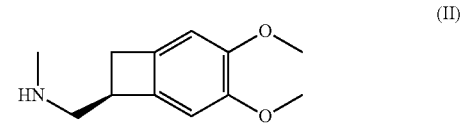

(II)

comprising the steps:
b) treatment of said mixture with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

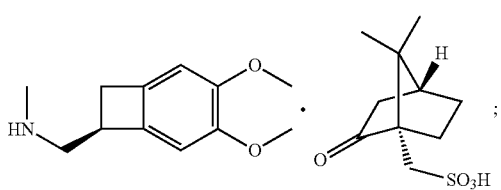

(IV)

c) separation of the salt of the compound of formula (IV) from the reaction media comprising ivabradine base;
d) isolation of ivabradine base from the solution resulting from step c)
e) optionally converting ivabradine base to the desired salt by addition of the corresponding acid in a suitable solvent (S1).

In one embodiment of the present invention the mixture comprising ivabradine base and (S)—N-[4,5-dimethoxybenzocyclobut-1-yl)-methyl] N-methylamine of formula (II) is dissolved or suspended in a suitable solvent (S2). Examples of suitable solvents (S2) are ketones such as acetone and methyl ethyl ketone; alcohols such as methanol, ethanol and isopropanol; nitriles such as acetonitrile; ethers such as tetrahydrofuran; esters such as ethyl acetate, toluene and the like or mixtures thereof.

In another embodiment of the present invention (1S)-(+)-10 camphorsulfonic acid is dissolved in a suitable solvent (S3) prior to its addition to the mixture of ivabradine and compound of formula (II). Examples of suitable solvents (S3) are ketones such as acetone and methyl ethyl ketone; alcohols such as methanol, ethanol and isopropanol; nitriles such as acetonitrile; ethers such as tetrahydrofuran; esters such as ethyl acetate, and the like or mixtures thereof, or mixtures of the solvents (S3) mentioned above with toluene.

In one embodiment of the present invention step b) is carried out at a temperature comprised between 0° C. and 30° C., for example between 20° C. and 25° C., between 10° C. and 15° C. or between 0° C. and 5° C.

In one embodiment of the present invention separation of the salt of the compound of formula (IV) from the reaction media comprising ivabradine base is carried out by a process selected from centrifugation and filtration. Filtration may be carried out using, by way of illustration and not limitation, one or more of membrane filtration, surface filtration, depth filtration, screen filtration, and filtration aid, for example.

Isolation of ivabradine base from the solution resulting from step c) may be carried out by concentrating in vacuo to dryness or alternatively adjusting the volume of solvent, or mixtures of solvents, for the next transformation.

Conversion of ivabradine base to the desired salt is carried out by addition of the corresponding acid in a suitable solvent or solvent mixture (S1). Suitable solvents (S1) include but are not limited to ketones such as acetone; alcohols such as methanol, ethanol and isopropanol; nitriles such as acetonitrile; ethers such as tetrahydrofuran; halogenated hydrocarbons such as dichloromethane, dichloroethane and chloroform; esters such as ethyl acetate, toluene, and the like or mixtures thereof.

The mixture comprising ivabradine base and at least (S)—N-[4,5-dimethoxybenzocyclobut-1-yl)-methyl] N-methylamine of formula (II) of step a) may be obtained by any suitable method. Advantageously it is obtained by method involving the preparation of ivabradine by condensation of a suitable precursor with (S)—N-[4,5-dimethoxybenzocyclobut-1-yl)-methyl] N-methylamine of formula (II).

In one embodiment the mixture comprising ivabradine base and at least (S)—N-[4,5-dimethoxybenzocyclobut-1-yl)-methyl] N-methylamine of formula (II) is obtained by a method comprising the steps:
a) condensation, optionally under reductive conditions, of (S)—N-[4,5-dimethoxybenzocyclobut-1-yl)-methyl] N-methylamine of formula (II)

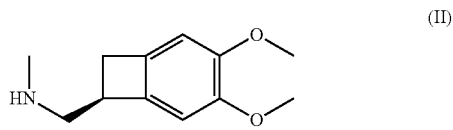

(II)

with a compound of formula (III)

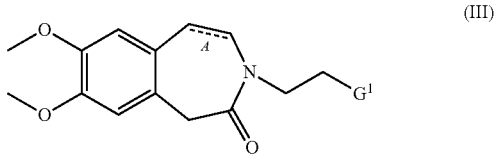

wherein the bond labeled with the letter A is either a single bond or a double bond, $G^1$ is selected from the group comprising —CH$_2$—X (being X an halogen atom, hydroxy, benzenesulfonyloxy, tosyloxy or methanesulfonyloxy group), a —CHO group, a —CN group and a —CH(OR$^1$) (OR$^2$) group wherein $R^1$ and $R^2$ are independently C1-C8 alkyl groups or $R^1$ and $R^2$ form together a C2-C4 alkylene or a C2-C4 alkenylene group, b) hydrogenation of the condensation product in the case where the bond labeled with the letter A is a double bond.

In an embodiment of the present invention compound of formula (III) is selected so that the bond labelled with the letter A is a single bond and $G^1$ is a group —CH$_2$—X wherein X is an halogen atom. In a preferred embodiment the reaction of compounds (II) and (III) as defined in the previous sentence is carried out in the presence of a base in polar aprotic or protic solvents. The base can be selected from triethylamine and alkali metal carbonates, bicarbonates and hydroxides and preferably potassium carbonate. The polar aprotic or protic solvent may be selected from tetrahydrofuran, toluene, acetone, acetonitrile, dimethylformamide, dimethylsulfoxide, N-methyl-2-pyrrolidone, water, isopropanol, C1-C4 linear aliphatic alcohols such as methanol, ethanol etc. and mixtures thereof. More preferably, the solvent is dimethylformamide or dimethylsulfoxide or mixtures of dimethylformamide with toluene and most preferably the solvent is dimethylformamide or mixtures of dimethylformamide with toluene. It is advantageous to use dimethylformamide during condensation reaction because reaction rate is faster. Reaction is conducted at 25-95° C. and preferably at 55-75° C. The completion of reaction can be monitored by high performance liquid chromatography.

In an embodiment of the present invention compound of formula (III) is selected so that the bond labelled with the letter A is a single bond and $G^1$ is selected from the group comprising a —CHO group and a —CH(OR$^1$) (OR$^2$) group wherein $R^1$ and $R^2$ are independently C1-C3 alkyl groups or $R^1$ and $R^2$ form together a C2-C4 alkylene or a C2-C4 alkenylene group. In a preferred embodiment the reductive amination reaction of compounds (II) and (III) as defined in the previous sentence is carried out in the presence of hydrogen an a suitable catalyst. Among the catalysts which can be used in the reductive amination, there may be mentioned, without implying any limitation, palladium, platinum, nickel, ruthenium, rhodium, and their compounds, particularly in supported form or in oxide form, preferably palladium-on-carbon. The temperature of the reductive amination reaction is preferably from 30 to 120° C., more preferably from 40 to 100° C., even more preferably from 60 to 95° C. The hydrogen pressure during the reductive amination reaction is preferably from 1 to 220 bars, more preferably from 1 to 100 bars, even more preferably from 10 to 60 bars.

Another aspect of the present invention is the use of compound (IV) to retrieve the excess of (S)—N-[4,5-dimethoxybenzocyclobut-1-yl)-methyl] N-methylamine of formula (II) present in the reaction mixture resulting from the condensation, optionally under reductive conditions, of (S)—N-[4,5-dimethoxybenzocyclobut-1-yl)-methyl] N-methylamine of formula (II)

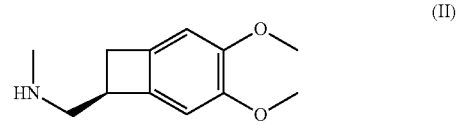

with a compound of formula (III)

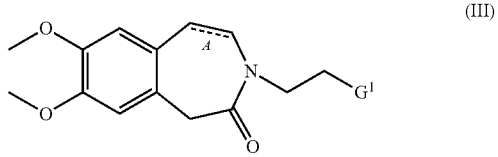

wherein the bond labeled with the letter A is either a single bond or a double bond, $G^1$ is selected from the group comprising —CH$_2$—X (being X an halogen atom, hydroxy, benzenesulfonyloxy, tosyloxy or methanesulfonyloxy group), a —CHO group, a —CN group and a —CH(OR$^1$) (OR$^2$) group wherein $R^1$ and $R^2$ are independently C1-C8 alkyl groups or $R^1$ and $R^2$ form together a C2-C4 alkylene or a C2-C4 alkenylene group followed by hydrogenation of the condensation product in the case where the bond labeled with the letter A is a double bond in a process to prepare ivabradine through the conversion of compound (IV) to compound (II) which may then be reused in the manufacture of ivabradine.

Another aspect of the present invention is the polymorphic form I of compound of formula (IV).

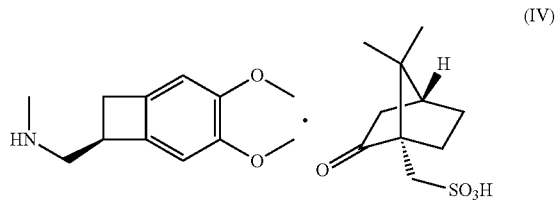

characterized in that its X-ray diffraction diagram, measured with a copper X-ray source has characterizing peaks (2 theta measured in degrees) at 7.20±0.2, 14.09±0.2, 14.24±0.2, 15.12±0.2, 17.69±0.2 and 18.78±0.2.

In one embodiment the X-ray diffraction diagram (measured with a copper X-ray source) of polymorphic form I of compound of formula (IV) additionally has characterizing peaks (2 theta measured in degrees) at 17.41±0.2, 19.07±0.2, 21.09±0.2, 22.29±0.2, 24.01±0.2 and 25.71±0.2.

PXRD analyses: The powder samples were sandwiched between polyester films of 20 micrometers of thickness and analysed in a PANalytical X'Pert PRO MPD theta/theta powder diffractometer of 240 millimeters of radius, in a configuration of convergent beam with a focalizing mirror and a flat sample transmission geometry, in the following experimental conditions: Cu K α radiation (l=1.5418 Å); Work power: 45 kV and 40 mA; Incident beam slits defining a beam height of 0.4 millimeters; Incident and diffracted beam 0.02 radians Soller slits; PIXcel detector: Active length=3.347 Å°; 2 theta/theta scans from 2 to 40 2 theta measured in degrees with a step size of 0.026 degrees and a measuring time of 300 seconds per step.

For the purpose of this invention, for X-ray diffraction patterns, depending on the calibration, sample or instrumentation, peaks at 2 theta measured in degrees can shift up to ±0.2 degrees (error). In one embodiment, all peaks in X-ray diffraction pattern shift up to +0.2 degrees, or up to −0.2 degrees. An X-ray diffraction pattern or peaks within that error is considered the same or substantially similar.

EXAMPLES

Example 1: Preparation of Highly Pure Ivabradine Hydrochloride ((+)-3-[3-[N-[4,5-Dimethoxybenzo-cyclobutan-1(S)-ylmethyl]-N-methylamino]propyl]-7,8-dimethoxy-2,3,4,5-tetrahydro-1H-3-benzazepin-2-one Hydrochloride)

52.64 g of a mixture comprising 85.83% of ivabradine, 10.59% of (S)—N-[4,5-dimethoxybenzocyclobut-1-yl)-methyl] N-methylamine and 3.58% of other non-identified impurities (determined by HPLC) is dissolved in 270 mL of toluene and 50 mL of acetonitrile. After dissolution, 5.62 g of (1S)-(+)-10 camphorsulfonic acid were added. The mixture was stirred at room temperature for 1 hour (after 10 min. the salt of (1S)-(+)-10 camphorsulfonic acid with (S)—N-[4,5-dimethoxybenzocyclobut-1-yl)-methyl] N-methylamine of formula (IV) precipitated). The solid was filtered and washed with 20 mL of toluene.

4.73 g of white solid were obtained. The X-Ray Powder Diffraction Diagram of the solid is shown in FIG. 1.

The mother liquor containing ivabradine base was concentrated in vacuo to dryness and the residue was dissolved in 160 mL of toluene and 303 mL of acetonitrile and precipitated by the addition of 8 mL of HCl 37%. The mixture was cooled at 0-5° C. for 2 hours. The solid (ivabradine hydrochloride) was filtered and washed with 60 mL of cool acetonitrile. The HPLC analysis of the solid showed that it contains only 0.82% of the salt of (1S)-(+)-10 camphorsulfonic acid with (S)—N-[4,5-dimethoxybenzocyclobut-1-yl)-methyl] N-methylamine.

The invention claimed is:

1. A method for the preparation of ivabradine base and salts thereof comprising the steps of:
a) providing a starting mixture comprising ivabradine base and at least (S)—N-[4,5-dimethoxybenzocyclobut-1-yl)-methyl] N-methylamine of formula (II)

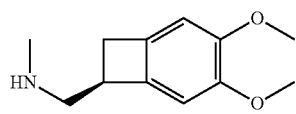

(II)

b) treatment of the mixture of step a) with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

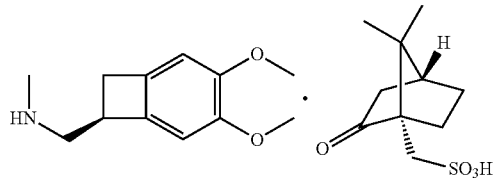

(IV)

c) separation of the salt of the compound of formula (IV) from the reaction media comprising ivabradine base;
d) isolation of ivabradine base from the solution resulting from step c)
e) optionally converting ivabradine base to the desired salt by addition of the corresponding acid in a suitable solvent (S1).

2. A method according to claim 1 wherein after step a) and before step b) the amount of (S)—N-[4,5-dimethoxybenzocyclobut-1-yl)-methyl] N-methylamine of formula (II) in the mixture of step a) is determined and wherein the amount of (1S)-(+)-10 camphorsulfonic acid used in step b) is selected so that the molar ratio of (1S)-(+)-10 camphorsulfonic acid to (S)—N-[4,5-dimethoxybenzocyclobut-1-yl)-methyl] N-methylamine of formula (II) is comprised between 0.5 and 1.5.

3. A method according to claim 1 wherein the mixture of step a) is dissolved or suspended in a solvent (S2) selected from the group consisting of acetone, methyl ethyl ketone, methanol, ethanol, isopropanol, acetonitrile, tetrahydrofuran, ethyl acetate, toluene and mixtures thereof.

4. A method according to claim 3 wherein the solvent (S2) is selected from toluene, acetonitrile and mixtures thereof.

5. A method according to claim 1 wherein (1S)-(+)-10 camphorsulfonic acid is dissolved, prior to its addition to the mixture of ivabradine and compound of formula (II), in a solvent (S3) selected from the group consisting of acetone, methyl ethyl ketone, methanol, ethanol, isopropanol, acetonitrile, tetrahydrofuran, ethyl acetate, and mixtures thereof, or mixtures of the above-mentioned solvents with toluene.

6. A method according to claim 5 wherein the solvent (S3) is selected from acetonitrile and mixtures of acetonitrile with toluene.

7. A method according to claim 1 wherein step b) is carried out at a temperature comprised between 0° C. and 30° C.

8. A method according to claim 7 wherein step b) is carried out at a temperature comprised between 20° C. and 25° C.

9. A method according to claim 1 wherein step c) wherein separation is carried out using one or more of membrane filtration, surface filtration, depth filtration, screen filtration and filtration aid.

10. A method according to claim 1 wherein isolation of ivabradine base from the solution resulting from step c) may be carried out by concentrating in vacuo to dryness or alternatively by adjusting the volume of solvent, or mixtures of solvents, for the next transformation.

11. A method according to claim 1 wherein ivabradine base is converted to its hydrochloride salt, by addition of the hydrochloric acid in a suitable solvent (S1).

12. A method for the purification of mixtures comprising ivabradine base and (S)—N-[4,5-dimethoxybenzocyclobut-1-yl)-methyl] N-methylamine of formula (II)

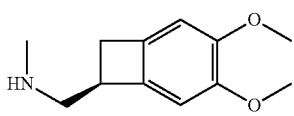

comprising the steps:
b) treatment of said mixture with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

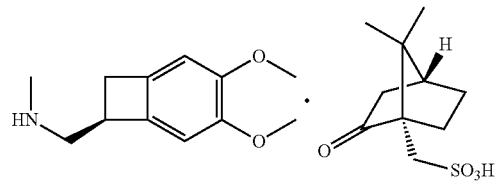

c) separation of the salt of the compound of formula (IV) from the reaction media comprising ivabradine base;
d) isolation of ivabradine base from the solution resulting from step c)
e) optionally converting ivabradine base to the desired salt by addition of the corresponding acid in a suitable solvent (S1).

13. A method for retrieving the excess of (S)—N-[4,5-dimethoxybenzocyclobut-1-yl)-methyl] N-methylamine of formula (II) present in the reaction mixture resulting from:
a) the condensation, optionally under reductive conditions, of (S)—N-[4,5-dimethoxybenzocyclobut-1-yl)-methyl] N-methylamine of formula (II)

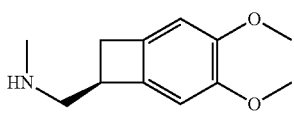

with a compound of formula (III)

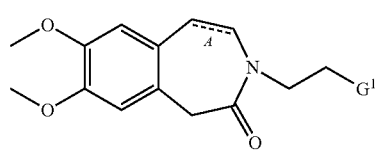

wherein the bond labeled with the letter A is either a single bond or a double bond, $G^1$ is selected from the group comprising $CH_2$—X (being X an halogen atom, hydroxy, benzenesulfonyloxy, tosyloxy or methanesulfonyloxy group), a CHO group, a —CN group and a —$CH(OR^1)(OR^2)$ group wherein $R^1$ and $R^2$ are independently C1-C8 alkyl groups or $R^1$ and $R^2$ form together a C2-C4 alkylene or a C2-C4 alkenylene group followed by hydrogenation of the condensation product in the case where the bond labeled with the letter A is a double bond, and b) treatment of the mixture of step a) with (1S)-(+)-10 camphorsulfonic acid to yield a mixture comprising ivabradine base and the salt of (1S)-(+)-10 camphorsulfonic acid with (S)—N-[4,5-dimethoxybenzocyclobut-1-yl)-methyl] N-methylamine of formula (IV)

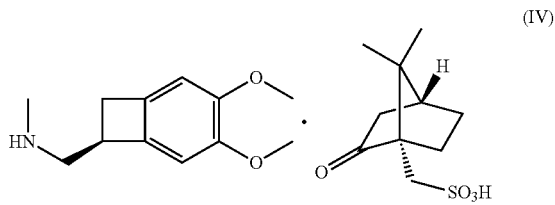

through the conversion of compound (IV) to compound (II), wherein said compound of formula (II) may then be reused in the manufacture of ivabradine.

14. Polymorphic form I of compound of formula (IV):

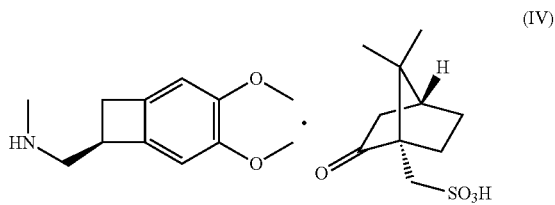

characterized in that its X-ray diffraction diagram, measured with a copper X-ray source has characterizing peaks (2 theta) at 7.20±0.2, 14.09±0.2, 14.24±0.2, 15.12±0.2, 17.69±0.2 and 18.78±0.2, and also having characterizing peaks (2 theta) at 17.41±0.2, 19.07±0.2, 21.09±0.2, 22.29±0.2, 24.01±0.2 and 25.71±0.2.

15. A method according to claim 2 wherein the mixture of step a) is dissolved or suspended in a solvent (S2) selected from the group consisting of acetone, methyl ethyl ketone, methanol, ethanol, isopropanol, acetonitrile, tetrahydrofuran, ethyl acetate, toluene and mixtures thereof.

16. A method according to claim 15 wherein the solvent (S2) is selected from toluene, acetonitrile and mixtures thereof.

17. A method according to claim 2 wherein (1S)-(+)-10 camphorsulfonic acid is dissolved, prior to its addition to the mixture of ivabradine and compound of formula (II), in a solvent (S3) selected from the group consisting of acetone, methyl ethyl ketone, methanol, ethanol, isopropanol, acetonitrile, tetrahydrofuran, ethyl acetate, and mixtures thereof, or mixtures of the above-mentioned solvents with toluene.

18. A method according to claim 3 wherein (1S)-(+)-10 camphorsulfonic acid is dissolved, prior to its addition to the mixture of ivabradine and compound of formula (II), in a solvent (S3) selected from the group consisting of acetone, methyl ethyl ketone, methanol, ethanol, isopropanol, acetonitrile, tetrahydrofuran, ethyl acetate, and mixtures thereof, or mixtures of the above-mentioned solvents with toluene.

19. A method according to claim 4 wherein (1S)-(+)-10 camphorsulfonic acid is dissolved, prior to its addition to the mixture of ivabradine and compound of formula (II), in a solvent (S3) selected from the group consisting of acetone, methyl ethyl ketone, methanol, ethanol, isopropanol, acetonitrile, tetrahydrofuran, ethyl acetate, and mixtures thereof, or mixtures of the above-mentioned solvents with toluene.

* * * * *